United States Patent
Cordi et al.

(10) Patent No.: US 7,250,411 B2
(45) Date of Patent: Jul. 31, 2007

(54) BENZOTHIAZINE AND BENZOTHIADIAZINE COMPOUNDS

(75) Inventors: Alex Cordi, Suresnes (FR); Patrice Desos, Bois-Colombes (FR); Pierre Lestage, La Celle Saint Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 51 days.

(21) Appl. No.: 10/499,082

(22) PCT Filed: Dec. 20, 2002

(86) PCT No.: PCT/FR02/04484

§ 371 (c)(1),
(2), (4) Date: Jun. 15, 2004

(87) PCT Pub. No.: WO03/053947

PCT Pub. Date: Jul. 3, 2003

(65) Prior Publication Data

US 2005/0014744 A1   Jan. 20, 2005

(30) Foreign Application Priority Data

Dec. 21, 2001 (FR) ................................. 01 16622

(51) Int. Cl.
C07D 285/22 (2006.01)
A61K 31/5415 (2006.01)
A61P 25/24 (2006.01)

(52) U.S. Cl. ..................... 514/223.2; 544/12
(58) Field of Classification Search .................. 544/12; 514/223.2
See application file for complete search history.

(56) References Cited

FOREIGN PATENT DOCUMENTS

| WO | WO 9321170 | 10/1993 |
| WO | WO 9812185 | 3/1998 |
| WO | WO 9942456 | 8/1999 |
| WO | WO 9942456 A2 * | 8/1999 |
| WO | WO 0140210 | 7/2001 |

OTHER PUBLICATIONS

Alt et al. Current Pharmaceutical Design, 2005, 11, 1511-1527.*
Black et al Psychopharmacology (2005) 179: 154-163.*
Phillips et al. Bioorganic & Medicinal Chemistry 10 (2002) 1229-1248.*
Maskell, et al., *Br. J. Pharmacol*, 2003, 140, 1313-1319.
Aracava, et al., *JPET*, 2005, 312, 1195-1250.
Advokat, et al., *Neurosci. Biobehav. Rev.*, 1992, 16, 13-24.
Danysz, et al., *Behav. Pharmacol.*, 1995, 6, 455-474.
Lynch, *Neurobiology of Learning and Memory*, 1998, 70, 82-100.
Robbins, et al., *TRENDS in Pharmacological Sciences*, 2006, 27 (3), 141-148.
Bliss, et al., *Nature*, 1993, 361, 31-39.
Ito, et al., *Journal of Physiology*, 1990, 424, 533-543.
Cumin, et al., *Psychopharmacology*, 1982, 78, 104-111.
Arai, et al., *Brain Res.*, 1994, 638, 343-346.
Miu, et al., *Neuropharmacol.*, 2001, 40, 976-983.
Staubli, et al., *Proc. Natl. Acad. Sci.*, 1994, 91, 777-781.
Lebrun, et al., *European Journal of Pharmacology*, 2000, 401, 205-212.
Rao, et al., *Neuroscience Letters*, 2001, 298, 183-186.
Thompson, et al., *Proc. Natl. Acad. Sci.*, 1995, 92, 7667-7671.
Buccafusco, et al., *Neuropharmacol.*, 2004, 46, 10-22.
Porrino, et al., *PLOS Biology*, 2005, 3 (9), 1639-1652.
Ingvar, et al., *Exp. Neurol.*, 1997, 146, 553-559.
Lynch, et al., *Exp. Neurol.*, 1997, 145, 89-92.
Baudry, *Neurobiology of Learning and Memory*, 2001, 76, 284-297.
Day, et al., *Nature*, 2003, 424, 205-209.
Lynch, *Current Opinion in Pharmacology*, 2006, 6, 82-88.
Lin, et al., *Brain Research*, 2002, 955, 164-173.
Desai, et al., *Neuropharmacology*, 1995, 34 (2), 141-147.
Lockhart, et al., *European Journal of Pharmacology*, 2000, 401, 145-153.
Jhee, et al., *J. Clin. Pharmacol.*, 2006, 46, 424-432.
Roger, et al., *Soc. Neurosci. Abstr.*, 2004, Abstract No. 219.11.

(Continued)

*Primary Examiner*—Kahsay Habte
(74) *Attorney, Agent, or Firm*—Hueschen and Sage

(57) ABSTRACT

Compounds of formula (I):

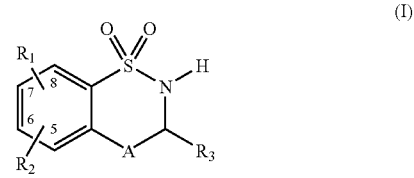

wherein:
$R_1$ represents hydroxy or RCO—O—,
$R_2$ represents hydrogen, halogen, hydroxy or R'CO—O,
R, R', which may be identical or different, represent linear or branched ($C_1$-$C_6$)alkyl optionally substituted by aryl, linear or branched ($C_2$-$C_6$)alkenyl optionally substituted by aryl, linear or branched ($C_1$-$C_6$)perhaloalkyl, ($C_3$-$C_7$)cycloalkyl, adamantyl, aryl or heteroaryl,
$R_3$ represents hydrogen, linear or branched ($C_1$-$C_6$)alkyl or ($C_3$-$C_7$)cycloalkyl,
A represents $CR_4R_5$ or $NR_4$, $R_4$ represents hydrogen or linear or branched ($C_1$-$C_6$)alkyl, their isomers and also their addition salts with a pharmaceutically acceptable acid or base.

Medicaments.

8 Claims, No Drawings

OTHER PUBLICATIONS

Dicou, et al., *Brain Research*, 2003, 970, 221-225.
Bahr, et al., *Exp. Neurol.*, 2002, 174, 37-47.
Murray, et al., *JPET*, 2003, 306, 752-762.
O'Neill, et al., *European Journal of Pharmacology*, 2004, 486, 163-174.
O'Neill, et al., *CNS Drug Rev.*, 2005, 11 (1), 77-96.
Bai, et al., *Neuropharmacology*, 2003, 44, 1013-1021.
Lauterborn, et al., *J. of Neuroscience*, 2000, 20 (1), 8-21.
Carrie, et al., *Soc. Neurosci. Abstr.*, 2005, Abstract No. 1018.4.
Lockhart, et al., *Soc. Neurosci. Abstr.*, 2004, Abstract No. 92.12.
Munoz, et al., *Soc. Neurosci. Abstr.*, 2004, Abstract No. 85.13.
Nibuya, et al., *J. of Neuroscience*, 1995, 15 (11), 7539-7547.
Dias, et al., *Neuropharmacology*, 2003, 45, 553-563.
Alt, et al., *Curr. Pharm. Des.*, 2005, 11 (12), 1511-1527.
Alt, et al., *Biochemical Pharmacology*, 2006, 71, 1273-1288.
Nakamura, et al., *Psychopharmacology*, 2001, 158, 205-212.
Li, et al., *Neuropharmacology*, 2001, 40, 1028-1033.
Knapp, et al., *European Journal of Pharmacology*, 2002, 440, 27-35.

* cited by examiner

BENZOTHIAZINE AND BENZOTHIADIAZINE COMPOUNDS

The present invention relates to new benzothiazine and benzothiadiazine compounds, to a process for their preparation and to pharmaceutical compositions containing them.

It is now recognised that excitatory amino acids and, more especially, glutamate, play a crucial role in the physiological processes of neuronal plasticity and in the mechanisms underlying learning and memory. Pathophysiological studies have shown clearly that a deficiency in glutamatergic neurotransmission is closely associated with the development of Alzheimer's disease (Neuroscience and Biobehavioral reviews, 1992, 16, 13-24; Progress in Neurobiology, 1992, 39, 517-545).

Moreover, numerous studies over recent years have demonstrated the existence of excitatory amino acid receptor sub-types and their functional interactions (Molecular Neuropharmacology, 1992, 2, 15-31).

Among those receptors, the AMPA ("α-amino-3-hydroxy-5-methyl-4-isoxazole-propionic acid") receptor appears to be the receptor most implicated in the phenomena of physiological neuronal excitability and especially in those phenomena implicated in the processes of memorisation. For example, learning has been shown to be associated with an increase in the binding of AMPA to its receptor in the hippocampus, one of the cerebral regions essential to mnemocognitive processes. Similarly, nootropic agents, such as aniracetam, have very recently been described as modulating positively the AMPA receptors of neuronal cells (Journal of Neurochemistry, 1992, 58, 1199-1204).

In the literature, compounds of benzamide structure have been described as having that same mechanism of action and as improving mnesic performance (Synapse, 1993, 15, 326-329). Compound BA 74, in particular, is the most active of those new pharmacological agents. facilitatory action on AMPA flux and patent application WO 99/42456 describes, inter alia, a number of benzothiadiazine compounds as modulators of AMPA receptors.

In addition to being new, the benzothiazine compounds forming the subject-matter of the present invention surprisingly exhibit pharmacological activities in respect of AMPA flux that are clearly superior to those of the compounds of similar structure described in the prior art. They are useful as AMPA modulators in the treatment or prevention of mnemocognitive disorders associated with age, with anxiety or depressive syndromes, with progressive neurogenerative diseases, with Alzheimer's disease, with Pick's disease, with Huntington's chorea, with schizophrenia, with sequelae of acute neurodegenerative diseases, with sequelae of ischaemia and with sequelae of epilepsy.

The present invention relates more specifically to compounds of formula (I):

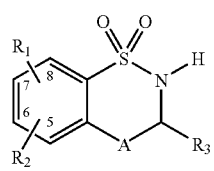

(I)

wherein
$R_1$ represents a hydroxy group or a RCO—O— group,
$R_2$ represents a hydrogen atom, a halogen atom, a hydroxy group or a R'CO—O— group,
R, R', which may be identical or different, represent a linear or branched ($C_1$-$C_6$)alkyl group optionally substituted by an aryl group, a linear or branched ($C_2$-$C_6$)alkenyl group optionally substituted by an aryl group, a linear or branched ($C_1$-$C_6$)perhaloalkyl group, a ($C_3$-$C_7$)cycloalkyl group, an adamantyl group, an aryl group or a heteroaryl group,
$R_3$ represents a hydrogen atom, a linear or branched ($C_1$-$C_6$)alkyl group or a ($C_3$-$C_7$)-cycloalkyl group,
A represents a $CR_4R_5$ group or an $NR_4$ group,
$R_4$ represents a hydrogen atom or a linear or branched ($C_1$-$C_6$)alkyl group,
$R_5$ represents a hydrogen atom or a halogen atom, to their isomers and to their addition salts with a pharmaceutically acceptable acid or base, it being understood that:
$R_1$ represents an RCO—O— group when it is located in the 5 position of the compound of formula (I),
"aryl group" is understood to mean an aromatic monocyclic group, or a bicyclic group in which at least one of the rings is aromatic, optionally substituted by one or more identical or different groups: halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$)perhaloalkoxy, hydroxy, cyano, nitro, amino (optionally substituted by one or more linear or branched ($C_1$-$C_6$)alkyl groups), aminosulphonyl (optionally substituted by one or more linear or branched ($C_1$-$C_6$)alkyl groups) or phenyl (optionally substituted by one or more identical or different groups: halogen, linear or branched ($C_1$-$C_6$)alkyl, linear or branched ($C_1$-$C_6$)perhaloalkyl, hydroxy or linear or branched ($C_1$-$C_6$)alkoxy),
"heteroaryl group" is understood to mean an aromatic monocyclic group, or a bicyclic group in which at least one of the rings is aromatic, containing one, two or three identical or different hetero atoms selected from nitrogen, oxygen and sulphur, optionally substituted by one or more identical or different groups: halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$)perhaloalkoxy, hydroxy, cyano, nitro, amino (optionally substituted by one or more linear or branched ($C_1$-$C_6$)alkyl groups) or aminosulphonyl (optionally substituted by one or more linear or branched ($C_1$-$C_6$)-alkyl groups).

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

Preferred aryl groups are optionally substituted phenyl, naphthyl and tetrahydronaphthyl groups.

Preferred heteroaryl groups are optionally substituted pyridinyl, pyrrolyl, thienyl, furyl, imidazolyl and indolyl groups, and more especially pyridinyl, thienyl and furyl groups.

The group $R_1$ is preferably located in the 7 position of the compound of formula (I).

The group $R_2$ is preferably a hydrogen atom and preferred R groups are aryl and heteroaryl groups.

The invention relates also to a process for the preparation of compounds of formula (I).

The process for the preparation of compounds of formula (I) wherein A represents a $CR_4R_5$ group is characterised in that there is used as starting material a compound of formula (II):

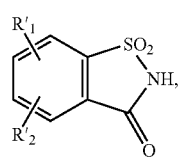
(II)

wherein:
$R'_1$ represents a linear or branched $(C_1-C_6)$alkoxy group,
$R'_2$ represents a hydrogen atom, a halogen atom or a linear or branched $(C_1-C_6)$alkoxy group, which is subjected to the action of chloroacetone in the presence of a mineral base in dimethylformamide medium to yield the compound of formula (III):

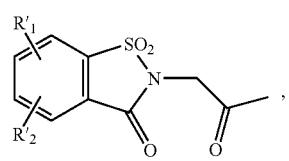
(III)

wherein $R'_1$ and $R'_2$ are as defined hereinbefore, which is subjected to rearrangement in basic medium to yield the compound of formula (IV):

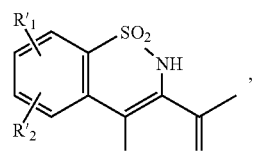
(IV)

wherein $R'_1$ and $R'_2$ are as defined hereinbefore, which is deacetylated by heating at reflux in benzene medium in the presence of an excess of ethylene glycol and a catalytic amount of p-toluenesulphonic acid to yield the compound of formula (V):

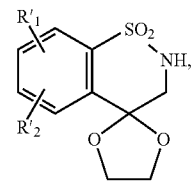
(V)

wherein $R'_1$ and $R'_2$ are as defined hereinbefore, which is subjected to hydrolysis in acid medium to yield the compound of formula (VIa):

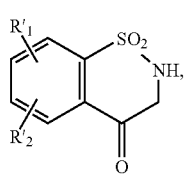
(VIa)

wherein $R'_1$ and $R'_2$ are as defined hereinbefore, of which, optionally, when $R_3$ is other than a hydrogen atom, the nitrogen atom is protected by a protecting group, and which then, after treatment with a strong base, is treated with a compound of formula $R'_3$—P, wherein $R'_3$ represents a linear or branched $(C_1-C_6)$alkyl group or a $(C_3-C_7)$cycloalkyl group and P represents a leaving group, to yield, after deprotection of the nitrogen atom, the compound of formula (VI'a)

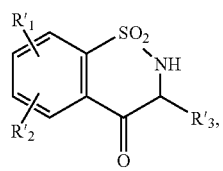
(VI'a)

wherein $R'_1$, $R'_2$ and $R'_3$ are as defined hereinbefore, which compound of formula (VIa) or (VI'a), represented by formula (VI):

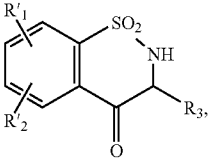
(VI)

wherein $R'_1$ and $R'_2$ have the same meaning and $R_3$ is as defined for formula (I), is:
either subjected to catalytic reduction to yield the compound of formula (VII):

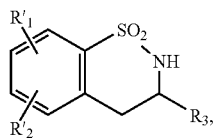
(VII)

wherein R'₁ and R'₂ are as defined hereinbefore,
or converted in alcohol by the action of a hydride the hydroxy group of which is converted to a halogen atom by the action of an appropriate reagent,
to yield the compound of formula (VIII):

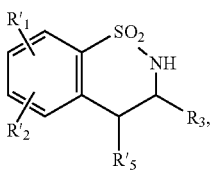
(VIII)

wherein R'₁ and R'₂ are as defined hereinbefore, R'₅ represents a halogen atom,
or subjected to the action of an organomagnesium compound R'₄ MgBr wherein R'₄ represents a linear or branched (C₁-C₆)alkyl group,
to yield the compound of formula (VIb):

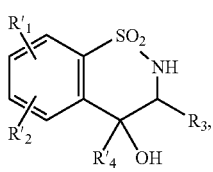
(VIb)

wherein R'₁, R'₂ and R'₄ are as defined hereinbefore,
which compound of formula (VIb):
is either subjected to catalytic reduction to yield the compound of formula (IX):

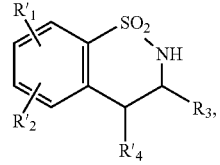
(IX)

wherein R'₁, R'₂ and R'₄ are as defined hereinbefore,
or the hydroxy group of which is converted to a halogen atom by the action of an appropriate reagent,
to yield the compound of formula (X):

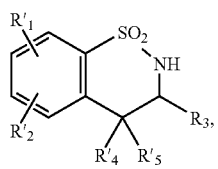
(X)

wherein R'₁, R'₂ and R'₄ are as defined hereinbefore and R'₅ represents a halogen atom,
the group R'₁ and the group R'₂, when it represents a linear or branched (C₁-C₆)alkoxy group, of which compounds of formulae (VII) to (X) are converted to hydroxy groups to yield the compound of formula (I/a), a particular case of the compounds of formula (I):

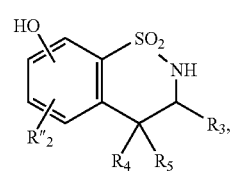
(I/a)

wherein R₄ and R₅ are as defined for formula (I) and R"₂ represents a hydrogen atom, a halogen atom or a hydroxy group,
the hydroxy function or functions of which compound of formula (I/a) are, if desired, converted to corresponding esters,
which compound of formula (I/a) and its corresponding esters, which constitute the totality of the compounds of formula (I),
are purified, if necessary, according to a conventional purification technique, are optionally separated into the isomers according to a conventional separation technique and are converted, if desired, into their addition salts with a pharmaceutically acceptable acid or base.

The process for the preparation of compounds of formula (I) wherein A represents an NR₄ group is characterised in that there is used as starting material a compound of formula (XI):

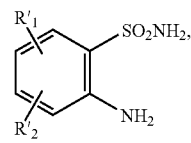
(XI)

wherein:
R'₁ represents a linear or branched (C₁-C₆)alkoxy group,
R'₂ represents a hydrogen atom, a halogen atom or a linear or branched (C₁-C₆)alkoxy group,
which is cyclised
either in the presence of an amidine of formula (XII):

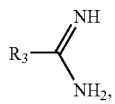

(XII)

wherein:
R₃ is as defined for formula (I),
to yield the compound of formula (XIII):

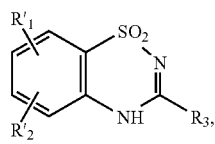

(XIII)

wherein $R'_1$, $R'_2$ and $R'_3$ are as defined hereinbefore,
which is:
either reduced with a metallic hydride to yield the compound of formula (XIV):

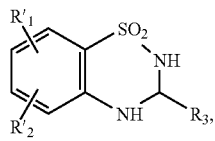

(XIV)

wherein $R'_1$, $R'_2$ and $R'_3$ are as defined hereinbefore,
or alkylated by the action of a strong base in the presence of an alkylating agent $R'_4X$ wherein $R'_4$ represents a linear or branched ($C_1$-$C_6$)alkyl group and X represents a halogen atom, and then reduced
to yield the compound of formula (XV):

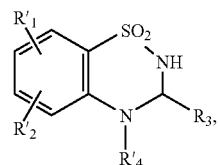

(XV)

wherein $R'_1$, $R'_2$, $R_3$ and $R'_4$ are as defined hereinbefore,
or cyclised in the presence of an aldehyde of formula (XVI):

(XVI)

wherein $R_3$ is as defined for formula (I),
to yield the compound of formula (XIV) described above, the group $R'_1$ and the group $R'_2$, when it represents a linear or branched ($C_1$-$C_6$)alkoxy group, of which compound of formula (XIV) or (XV) are converted to hydroxy groups to yield the compound of formula (I/b), a particular case of the compounds of formula (I):

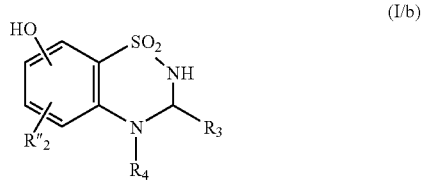

(I/b)

wherein $R_3$ and $R_4$ are as defined for formula (I) and $R''_2$ represents a hydrogen atom, a halogen atom or a hydroxy group,
the hydroxy function or functions of which compound of formula (I/b) are, if desired, converted to corresponding esters,
which compound of formula (I/b) and its corresponding esters, which constitute the totality of the compounds of formula (I),
are purified, if necessary, according to a conventional purification technique, are optionally separated into the isomers according to a conventional separation technique and are converted, if desired, into their addition salts with a pharmaceutically acceptable acid or base.

The invention extends also to pharmaceutical compositions comprising as active ingredient a compound of formula (I) with one or more appropriate inert, non-toxic excipients. Among the pharmaceutical compositions according to the invention there may be mentioned more especially those which are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions, etc. . . .

The dosage used can be adapted according to the nature and the severity of the disorder, the administration route and the age and weight of the patient. The dosage ranges from 1 to 5100 mg per day in one or more administrations.

The following Examples illustrate the invention but do not limit it in any way.

The starting materials used are known products or products prepared according to known procedures.

The structures of the compounds described in the Examples were determined according to customary spectrophotometric techniques (infra-red, NMR, mass spectrometry . . . ).

EXAMPLE 1

3,4-Dihydro-2H-1,2-benzothiazin-7-ol 1,1-dioxide

Step A: 6-Methoxy-2-(2-oxopropyl)-1,2-benzisothiazol-3 (2H)-one 1,1-dioxide 360 mg of 6-methoxy-1,1-dioxo-1,2-dihydro-benzo[d] isothiazol-3-one are added in small portions to a suspension of 72 mg of 60% NaH in mineral oil in 1.6 ml of anhydrous dimethylformamide. After stirring for 30 min. at ambient temperature, the reaction mixture becomes homogeneous and 162 µl of chloroacetone are added thereto. The reaction mixture is heated at 110° C. for 30 min. It is allowed to return to ambient temperature, and then the mixture is precipitated by addition of water. The precipitate is filtered off, rinsed several times with water, suction-filtered off and dried in vacuo.

Melting Point: 185-191° C.

Step B: 2-Acetyl-7-methoxy-2H-1,2-benzothiazin-4-ol 1,1-dioxide

A solution of sodium ethanolate in ethanol is prepared by dissolving 1.08 g of sodium in 23 ml of ethanol at reflux. The temperature of the solution is brought to 40° C. and 6.30 g of the product of Step A are added thereto with stirring. The reaction mixture becomes thicker. 5 ml of ethanol are added to allow stirring to be carried out, and heating for an additional 10 min. is carried out at 50-55° C. The reaction mixture is then cooled in an ice bath and acidified with 3N HCl and the yellow precipitate formed is filtered off.

Melting Point: 162-166° C.

Step C: 7-Methoxy-2,3-dihydro-4H-1,2-benzothiazine-4,4-ethylenedioxy 1,1-dioxide 5.35 g of the product obtained in the above Step, 200 mg of para-toluenesulphonic acid and 5.6 ml of ethylene glycol are stirred at reflux in 200 ml of benzene in a round-bottomed flask on which a Dean-Stark apparatus is mounted. After refluxing for 72 h, the benzene is evaporated off in vacuo. The residue is dissolved in ethyl acetate and the organic phase is washed with water and then with saturated NaCl. Drying, filtration and evaporation are carried out and an oil is obtained which is crystallised from an ethyl ether/isopropyl ether mixture.

Melting Point: 100-110° C.

Step D: 7-Methoxy-2,3-dihydro-4H-1,2-benzothiazin-4-one 1,1-dioxide

A solution of 2.63 g of the product of the above Step in a mixture of 50 ml of methanol and 50 ml of 3 N HCl is stirred at reflux for 15 min. The methanol is evaporated off in vacuo and the aqueous phase is extracted with ether. The organic phase is dried and treated with animal black. Following filtration and evaporation, the residue is taken up in isopropyl ether and the solid is filtered off.

Melting Point: 124-127° C.

Step E: 7-Methoxy-3,4-dihydro-2H-1,2-benzothiazine 1,1-dioxide 1.77 g of the product of the above Step in 40 ml of acetic acid is hydrogenated under 5 bar at 70° C. in the presence of 1.75 g of 10% Pd/C. The mixture is allowed to return to ambient temperature and the catalyst is filtered off. The filtrate is evaporated to dryness and the residue is chromatographed on silica, using a 95/5 methylene chloride/ethyl acetate system as eluant, to yield the expected product.

Melting Point: 144-145° C.

Step F: 3,4-Dihydro-2H-1,2-benzothiazin-7-ol 1,1-dioxide 14.1 ml of a 1 M solution of $BBr_3$ in methylene chloride are added dropwise to a solution of 1 g of the product of the above Step in 45 ml of methylene chloride cooled to −35° C. The mixture is allowed to return to ambient temperature. After stirring for 3 h at ambient temperature, the reaction mixture is poured into water at 5° C. and extraction is carried out with ethyl acetate. The organic phases are combined, washed with saturated NaCl, dried, filtered and evaporated. A solid is obtained which is taken up in a small amount of isopropyl ether. The title product is filtered off.

Melting Point: 173-177° C. Elemental Microanalysis:

|  | C | H | N | S |
|---|---|---|---|---|
| % theoretical | 48.23 | 4.55 | 7.03 | 16.09 |
| % experimental | 48.53 | 4.54 | 7.16 | 15.82 |

EXAMPLE 2

1,1-Dioxido-3,4-dihydro-2H-1,2-benzothiazin-7-yl benzoate

The expected product is obtained by benzoylation of the compound of Example 1 with benzoic acid chloride in dichloromethane in the presence of 1.5 eq. of triethylamine and a catalytic amount of dimethylaminopyridine.

Melting Point: 153-156° C. Elemental Microanalysis:

|  | C | H | N | S |
|---|---|---|---|---|
| % theoretical | 59.39 | 4.32 | 4.62 | 10.57 |
| % experimental | 59.48 | 4.38 | 4.69 | 10.67 |

EXAMPLE 3

3-Methyl-1,1-dioxido-3,4-dihydro-2H-1,2,4-benzothiadiazin-7-yl benzoate

Step A: 7-Methoxy-3-methyl-3,4-dihydro-2H-1,2,4-benzothiadiazine 1,1-dioxide

829 µl of acetaldehyde are added to a suspension of 20 g of 2-amino-5-methoxy-benzenesulphonamide in 20 ml of anhydrous ethanol. The reaction mixture becomes homogeneous and is heated at reflux for 30 min. The ethanol is evaporated off in vacuo. The solid is taken up in ether and filtered off. The solid is taken up in 40 ml of ethanol, refluxed for 15 min. and allowed to return to ambient temperature. The expected product is obtained after filtration.

Melting Point: 208-218° C.

Step B: 3-Methyl-3,4-dihydro-2H-1,2,4-benzothiadiazin-7-ol 1,1-dioxide 1.76 ml of $BBr_3$ is added dropwise to a suspension of 1.70 g of the product of the above Step in 85 ml of methylene chloride cooled to −65 ° C. The reaction mixture is stirred for 45 min. at −65° C. and then the temperature is allowed to return to ambient temperature. After 3 h at ambient temperature, the mixture is poured onto ice. When the ice has melted, the aqueous phase is extracted with ethyl acetate. The organic phases are combined, washed and dried. The expected product is purified by chromatography on silica using a 98/2 methylene chloride/methanol system as eluant.

Melting Point: 210-212° C.

Step C: 3-Methyl-1,1-dioxido-3,4-dihydro-2H-1,2,4-benzothiadiazin-7-yl benzoate

The expected product is obtained by benzoylation of the product described in Step B with benzoic acid chloride in dichloromethane in the presence of 1.5 eq. of triethylamine and a catalytic amount of dimethylaminopyridine.

Melting Point: 209-211° C. Elemental Microanalysis:

|  | C | H | N | S |
|---|---|---|---|---|
| % theoretical | 56.59 | 4.43 | 8.80 | 10.07 |
| % experimental | 56.56 | 4.43 | 8.68 | 10.25 |

EXAMPLE 4

4-Methyl-3,4-dihydro-2H-1,2,4-benzothiadiazin-7-ol 1,1-dioxide

Step A: 7-Methoxy-4H-1,2,4-benzothiadiazine 1,1-dioxide

A suspension of 3.0 g of 2-amino-5-methoxy-benzenesulphonamide is stirred for 1 night at 80° C. in the presence of 1.31 g of formamidine hydrochloride and 2.27 ml of triethylamine in 50 ml of toluene. The toluene is evaporated off in vacuo. The residue is taken up in water and the precipitate is filtered off.

Melting Point: 253-257° C.

Step B: 7-Methoxy-4-methyl-4H-1,2,4-benzothiadiazine 1,1-dioxide 2.88 g of the product obtained in the above Step are added, portion by portion, to a suspension of 9 ml of DMF containing 570 mg of 60% NaH in mineral oil. Stirring is carried out for 30 min. until a black solution is obtained. 929 μl of iodomethane are then added dropwise thereto. Stirring is continued for 1 h and the reaction mixture is precipitated by adding water. The precipitate is filtered off and rinsed with water and then with ether to yield the expected product.

Melting Point: 205-209° C.

Step C: 7-Methoxy-4-methyl-3,4-dihydro-2H-1, 2,4-benzothiadiazine 1,1-dioxide 1.19 g of sodium borohydride are added to a suspension of 2.37 g of the product of the above Step in 40 ml of ethanol. The mixture gradually becomes homogeneous. After reaction at ambient temperature for 1 h, the mixture is cooled in an ice bath and neutralised by the addition of 1N HCl. The white precipitate is stirred for 15 min. and the title product is filtered off.

Melting Point: 126-128° C.

Step D: 4-Methyl-3,4-dihydro-2H-1,2,4-benzothiadiazin-7-ol 1,1-dioxide 79.3 mmol of boron tribromide are added dropwise to a suspension containing 2 g of the product obtained in the above Step in 200 ml of dichloromethane maintained at −60° C. under nitrogen. The temperature is maintained for one hour and then the whole returns to ambient temperature and is stirred overnight. After cooling the reaction mixture in an ice bath, 100 ml of water are added and the biphasic system is stirred vigorously. The suspension thereby formed is filtered. The solid obtained is washed with water, with ether and dried, yielding the expected product.

Melting Point: 168-172° C. Elemental Microanalysis:

|  | C | H | N | S |
|---|---|---|---|---|
| % theoretical | 44.85 | 4.70 | 13.08 | 14.97 |
| % experimental | 45.10 | 4.83 | 12.64 | 14.77 |

EXAMPLE 5

4-Methyl-1,1-dioxido-3,4-dihydro-2H-1,2,4-benzothiadiazin-7-yl benzoate

The expected product is obtained by benzoylation of the compound of Example 4 with benzoic acid chloride in dichloromethane in the presence of 1.5 eq. of triethylamine and a catalytic amount of dimethylaminopyridine.

Melting Point: 199-201° C. Elemental Microanalysis:

|  | C | H | N | S |
|---|---|---|---|---|
| % theoretical | 56.59 | 4.43 | 8.80 | 10.07 |
| % experimental | 56.71 | 4.37 | 8.56 | 10.03 |

EXAMPLE 6

4-Ethyl-3,4-dihydro-2H-1,2,4-benzothiadiazin-7-ol 1,1-dioxide

The expected product is obtained according to the procedure described in Example 4 replacing iodomethane with iodoethane in Step B.

Melting Point: 214-218° C. Elemental Microanalysis:

|  | C | H | N | S |
|---|---|---|---|---|
| % theoretical | 47.36 | 5.30 | 12.27 | 14.05 |
| % experimental | 47.07 | 5.52 | 11.90 | 14.00 |

EXAMPLE 7

4-Ethyl-1,1-dioxido-3,4-dihydro-2H-1,2,4-benzothiadiazin-7-yl benzoate

The expected product is obtained by benzoylation of the compound of Example 6 with benzoic acid chloride in dichloromethane in the presence of 1.5 eq. of triethylamine and a catalytic amount of dimethylaminopyridine.

Melting Point: 148-152° C. Elemental Microanalysis:

|  | C | H | N | S |
|---|---|---|---|---|
| % theoretical | 57.82 | 4.85 | 8.43 | 9.65 |
| % experimental | 57.87 | 4.94 | 8.21 | 9.67 |

EXAMPLE 8

3-Cyclohexyl-3,4-dihydro-2H-1,2,4-benzothiadiazin-7-ol 1,1-dioxide

The product is obtained according to the procedure described in Example 3 by replacing acetaldehyde by cyclohexylcarboxaldehyde in Step A.

Melting Point: 268-273 °C. Elemental Microanalysis:

|  | C | H | N | S |
|---|---|---|---|---|
| % theoretical | 55.30 | 6.43 | 9.92 | 11.36 |
| % experimental | 54.81 | 6.38 | 9.44 | 11.12 |

EXAMPLE 9

3-Cyclohexyl-1,1-dioxido-3,4-dihydro-2H-1,2,4-benzothiadiazin-7-yl benzoate

The expected product is obtained by benzoylation of the compound of Example 8 with benzoic acid chloride in dichloromethane in the presence of 1.5 eq. of triethylamine and a catalytic amount of dimethylaminopyridine.

Melting Point: 214-218° C. Elemental Microanalysis:

|  | C | H | N | S |
|---|---|---|---|---|
| % theoretical | 62.16 | 5.74 | 7.25 | 8.3 |
| % experimental | 61.86 | 5.84 | 7.05 | 8.27 |

PHARMACOLOGICAL STUDY OF THE PRODUCTS OF THE INVENTION

Study of the Excitatory Fluxes Induced By AMPA in Xenopus oocytes a—Method:

mRNAs are prepared from cerebral cortex of male Wistar rat by the guanidinium thiocyanate/phenol/chloroform method. The poly-($A^+$) mRNAs are isolated by chromatography on oligo-dT cellulose and injected in an amount of 50 ng per oocyte. The oocytes are left to incubate for 2 to 3 days at 18° C. to allow expression of the receptors and are then stored at from 8 to 10° C.

Electrophysiological recording is carried out in a Plexiglass® chamber at from 20 to 24° C. in OR2 medium (J. Exp. Zool., 1973, 184, 321-334) by the 2-electrode "voltage-clamp" method, a 3rd electrode being placed in the bath to serve as reference.

All the compounds are administered via the incubation medium and the electric current is measured at the end of the period of administration. AMPA is used at a concentration of 10 µM. For each compound studied, the concentration that doubles (EC2X) or quintuples (EC5X) the intensity of the current induced by AMPA alone (5 to 50 nA) is determined.

b—Results:

The compounds of the invention potentiate very substantially the excitatory effects of AMPA and their activity is very clearly superior to that of the reference compounds.

The compound of Example 2 has, especially, an EC2X of 11.9 µM and a EC5X of 49.3 µM.

PHARMACEUTICAL COMPOSITION

Formulation for the preparation of 1000 tablets each comprising a dose of 100 mg

| compound of Example 1 | 100 g |
|---|---|
| hydroxypropyl cellulose | 2 g |
| wheat starch | 10 g |
| lactose | 100 g |
| magnesium stearate | 3 g |
| talc | 3 g |

The invention claimed is:

1. A compound selected from those of formula (I):

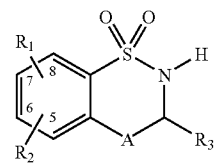

wherein:

$R_1$ represents hydroxy or RCO—O—, $R_2$ represents hydrogen, halogen, hydroxy or R'CO—O—, R and R', which may be identical or different, represent linear or branched ($C_1$-$C_6$)alkyl optionally substituted by aryl, linear or branched ($C_2$-$C_6$)alkenyl optionally substituted by aryl, linear or branched ($C_1$-$C_6$)perhaloalkyl, ($C_3$-$C_7$)cycloalkyl, adamantyl, aryl or heteroaryl, $R_3$ represents hydrogen, linear or branched ($C_1$-$C_6$)alkyl or ($C_3$-$C_7$)cycloalkyl, A represents $NR_4$, $R_4$ represents hydrogen or linear or branched ($C_1$-$C_6$) alkyl, its isomers and addition salts thereof with a pharmaceutically acceptable acid or base, it being understood that:

$R_1$ represents RCO—O— when it is located in the 5 position of the compound of formula (I), "aryl" may be an aromatic monocyclic group or a bicyclic group in which at least one of the rings is aromatic, each of those groups being optionally substituted by one or more identical or different halogen, linear or branched ($C_1$-$C_6$)alkyl, linear or branched ($C_1$-$C_6$)alkoxy, linear or branched ($C_1$-$C_6$) perhaloalkyl, linear or branched ($C_1$-$C_6$)-perhaloalkoxy, hydroxy, cyano, nitro, amino (optionally substituted by one or more linear or branched ($C_1$-$C_6$)alkyl), aminosulphonyl (optionally substituted by one or more linear or branched ($C_1$-$C_6$)alkyl) or phenyl (optionally substituted by one or more identical or different halogen, linear or branched ($C_1$-$C_6$) alkyl, linear or branched ($C_1$-$C_6$)perhaloalkyl, hydroxy or linear or branched ($C_1$-$C_6$)alkoxy), "heteroaryl" may be an aromatic monocyclic group or bicyclic group in which at least one of the rings is aromatic, containing one, two or three identical or different hetero atoms selected from nitrogen, oxygen and sulphur, each of those groups being optionally substituted by one or more identical or different halogen, linear or branched ($C_1$-$C_6$)alkyl, linear or branched ($C_1$-$C_6$)alkoxy, linear or branched ($C_1$-$C_6$) perhaloalkyl, linear or branched ($C_1$-$C_6$)perhaloalkoxy, hydroxy, cyano, nitro, amino (optionally substituted by one or more linear or branched ($C_1$-$C_6$)alkyl) or aminosulphonyl (optionally substituted by one or more linear or branched ($C_1$-$C_6$)alkyl).

2. A compound of claim 1 wherein $R_1$ is located in the 7 position of compound of formula (I).

3. A compound of claim 1 wherein $R_1$ represents hydroxy.

4. A compound of claim 1 wherein $R_1$ represents RCO—O—.

5. A compound of claim 1 wherein $R_2$ represents hydrogen.

6. Compound of claim 1 which is 1,1-dioxido-3,4-dihydro-2H-1,2-benzothiazin-7-yl benzoate.

7. A pharmaceutical composition comprising as active principle an effective amount of a compound of claim 1, together with one or more pharmaceutically acceptable excipients or vehicles.

8. A method for treating a living animal body, including a human, afflicted with a condition selected from anxiety and depression, comprising the step of administering to the living animal body, including a human, an amount of a compound of claim 1 which is effective for alleviation of the condition.

* * * * *